(12) United States Patent
Al-Abed

(10) Patent No.: US 8,618,147 B2
(45) Date of Patent: *Dec. 31, 2013

(54) MODIFIED MACROPHAGE MIGRATION INHIBITORY FACTOR INHIBITORS

(71) Applicant: Yousef Al-Abed, Dix Hills, NY (US)

(72) Inventor: Yousef Al-Abed, Dix Hills, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,530

(22) Filed: Jan. 28, 2013

(65) Prior Publication Data

US 2013/0190369 A1    Jul. 25, 2013

Related U.S. Application Data

(63) Continuation of application No. 12/225,571, filed as application No. PCT/US2007/007319 on Mar. 23, 2007, now Pat. No. 8,362,053.

(60) Provisional application No. 60/785,898, filed on Mar. 24, 2006.

(51) Int. Cl.
    *C07D 261/04*    (2006.01)

(52) U.S. Cl.
    USPC ........................................... 514/378; 548/240

(58) Field of Classification Search
    None
    See application file for complete search history.

(56) References Cited

U.S. PATENT DOCUMENTS

| | | |
|---|---|---|
| 7,662,843 B2 | 2/2010 | Al-Abed |
| 7,928,130 B2 | 4/2011 | Al-Abed |
| 8,362,053 B2 * | 1/2013 | Al-Abed ...................... 514/378 |
| 2003/0008908 A1 | 1/2003 | Al-Abed |
| 2003/0195194 A1 | 10/2003 | Gaeta et al. |
| 2004/0204464 A1 | 10/2004 | Al-Abed |
| 2005/0250826 A1 | 11/2005 | Sielecki-Dzurdz et al. |
| 2008/0305118 A1 | 12/2008 | Al-Abed |
| 2009/0305118 A1 | 12/2009 | Kim |
| 2009/0318509 A1 | 12/2009 | Al-Abed |

FOREIGN PATENT DOCUMENTS

| | | |
|---|---|---|
| JP | 2004-534054 A | 11/2004 |
| WO | 2005/094329 A2 | 10/2005 |

OTHER PUBLICATIONS

Cheng et al. "Critical modificatins of the ISO-1 scaffold improve its potent inhibition of macrophage migration inhibitory factor (MIF) tautomerase activity."
Bioorganic & Medicinal Chemistry Letters 16 (2006) 3376-3379.
A Communication dated Apr. 9, 2010 for European Application No. 07 794 337.1
A Response to the Apr. 9, 2010 Comrnunicaiton, dated Oct. 13, 2010, for European Application No. 07 794 337.1.
Australian Office Action regarding patent application No. 2007230948, dated Jun. 23, 2011.
Bloisoterism by Patani et al. Chem. Rev/ 1996, vol. 96, vol. 96, p. 3147-3176.
A Office Action dated Mar. 5, 2013 for related Canadian Application No. 2,647,163.
A Office Action Preliminary Notice of Reasons for Rejections dated Aug. 28, 2012 for related Japanese Patent Application No. 2009-501591 and its English translation.

* cited by examiner

*Primary Examiner* — Kamal Saeed
(74) *Attorney, Agent, or Firm* — Amster, Rothstein & Ebenstein LLP

(57) ABSTRACT

Provided are various compounds of Formula I (I). Also provided are various compounds of Formula II (II). Also provided are pharmaceutical compositions comprising the above compounds. Additionally, methods of inhibiting macrophage migration inhibitory factor (MIF) activity in a mammal are provided, as are methods of treating or preventing inflammation in a mammal. Further provided are methods of treating a mammal having sepsis, septicemia, and/or endotoxic shock. Also provided are methods of treating a mammal having an autoimmune disease, and methods of treating a mammal having a tumor.

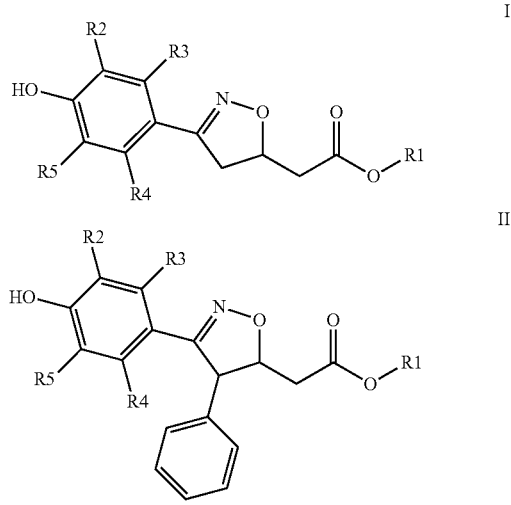

6 Claims, 6 Drawing Sheets

MODIFIED MACROPHAGE MIGRATION INHIBITORY FACTOR INHIBITORS

CROSS-REFERENCE TO RELATED APPLICATION

This application is a continuation of U.S. Ser. No. 12/225,571, filed Dec. 15, 2008 now U.S. Pat. No. 8,362,053, issued Jan. 29, 2013, which claims the benefit of U.S. Provisional Application No. 60/785,898, filed Mar. 24, 2006, the contents of each of which are hereby incorporated by reference.

BACKGROUND OF THE INVENTION

(1) Field of the Invention

The present invention relates to cytokine inhibitors. More specifically, the present invention identifies and characterizes several inhibitors of macrophage migration inhibitory factor.

(2) Description of the Related Art

Macrophage migration inhibitory factor (MIF) is a proinflammatory cytokine, critically involved in the pathogenesis of inflammatory disorders (Calandra and Roger, 2003; Riedemann et al., 2003). Recent studies have clearly defined MN as a critical factor in the pathophysiology of sepsis (Al-Abed et al., 2005). Abolition of MIF activity during sepsis by antibodies or ISO-1 improves cardio-circulatory efficiency and prevents the lethality associated with sepsis (Al-Abed et al., 2005; Lin et al., 2005). The specific inhibitor ISO-1, an isoxazoline, was designed to fit into the hydrophobic active site of MIF, an interaction confirmed by the crystal structure of the MIF complex with ISO-1 (FIG. 1) (Lubetsky et al., 2002). Administration of ISO-1 in a clinically relevant model of sepsis confers moderate protection (80% versus 40% control). These results identify ISO-1 as the first small molecule inhibitor of MIF proinflammatory activities with therapeutic implications and indicate the potential of the MIF active site as a novel target for therapeutic interventions in human sepsis. Based on the above, identification of other isoxazolines that inhibit MIF is desired. The present invention addresses that need.

SUMMARY OF THE INVENTION

The inventor has identified and characterized several new compounds that inhibit MIF activity.

The present invention is thus directed to compounds of Formula I:

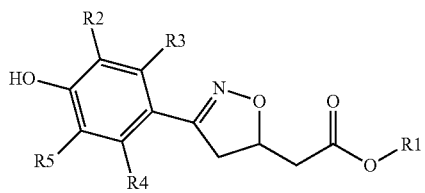

With these compounds, R1 is a straight or branched $C_1$-$C_{10}$ alkyl and R2, R3, R4 and R5 are independently F or H, wherein if all of R2, R3, R4 and R5 are H then R1 is not $CH_3$.

The invention is also directed to compounds of Formula II:

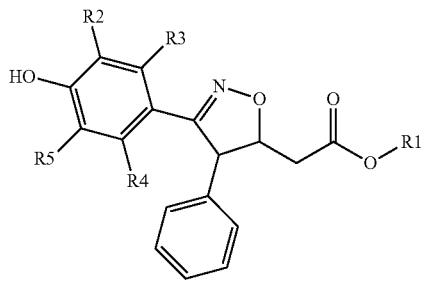

with these compounds R1 is a straight or branched $C_1$-$C_{10}$ alkyl, and R2, R3, R4 and R5 are independently F or H, provided that not all of R2, R3, R4 and R5 are H.

The invention is also directed to pharmaceutical compositions comprising any of the above compounds, or a pharmaceutically acceptable salt thereof, in a pharmaceutically acceptable carrier.

The present invention is additionally directed to methods of inhibiting macrophage migration inhibitory factor (MIF) activity in a mammal. The methods comprise administering the above pharmaceutical composition to the mammal in an amount effective to inhibit MT activity in the mammal.

Further, the invention is directed to methods of treating or preventing inflammation in a mammal. The methods comprise administering the above pharmaceutical composition to the mammal in an amount effective to treat or prevent the inflammation in the mammal.

Also, the present invention is directed to methods of treating a mammal having sepsis, septicemia, and/or endotoxic shock. The methods comprise administering the above pharmaceutical composition to the mammal in an amount effective to treat the sepsis, septicemia and/or endotoxic shock.

The invention is further directed to methods of treating a mammal having an autoimmune disease. The methods comprise administering the above pharmaceutical composition to the mammal in an amount effective to treat the autoimmune disease.

Additionally, the present invention is directed to methods of treating a mammal having a tumor, the method comprising administering the above pharmaceutical composition to the mammal in an amount effective to treat the tumor.

DETAILED DESCRIPTION OF THE INVENTION

Figure 1:
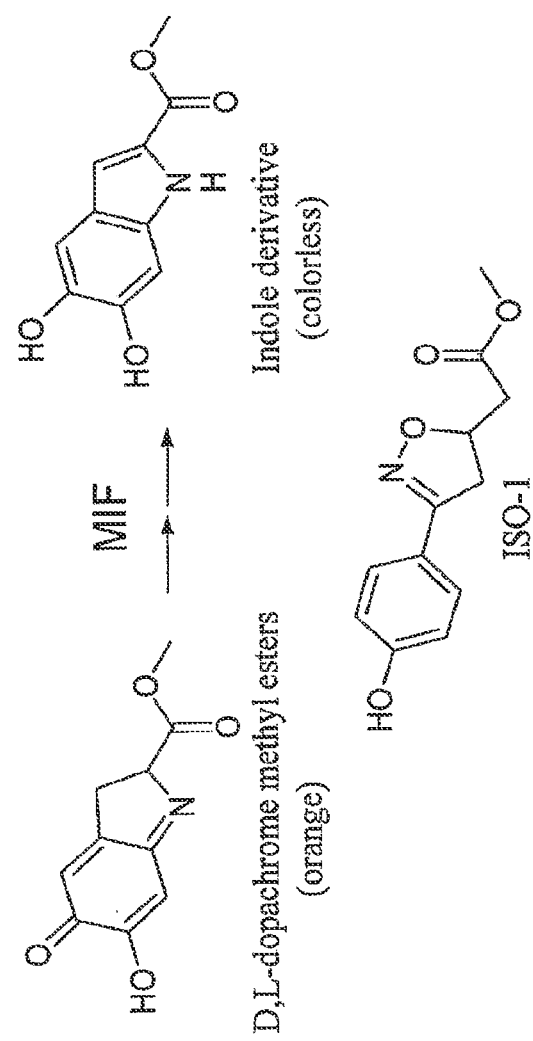
FIG. 1 shows a chemical pathway involving macrophage migration inhibitory factor (MIF), showing that MIF tautomerizes dopachrome methyl esters and also the structure of MIF inhibitor ISO-1.

The present invention provides several new compounds that inhibit MIF activity. See Examples.

The present invention is thus directed to compounds of Formula I:

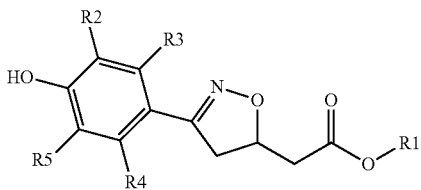

where R1 is a straight or branched $C_1$-$C_{10}$ alkyl and R2, R3, R4 and R5 are independently an F or H, wherein if all of R2, R3, R4 and R5 is H then R1 is not $CH_3$. Preferably, only one of R2, R3, R4 and R5 is F. More preferably, R2 is F.

With some preferred compounds, all of R2, R3, R4 and R5 are H. With other preferred compounds, R2 is F.

In additional preferred compounds, R1 is

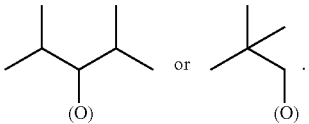

A more preferred compound is compound 17, having the formula

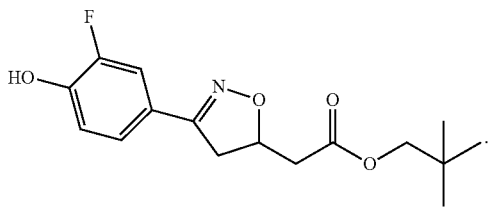 [SMILES: CC(C)(C)COC(=O)CC1CC(c2ccc(O)c(F)c2)=NO1]

An additional preferred compound is ISO-63, having the formula

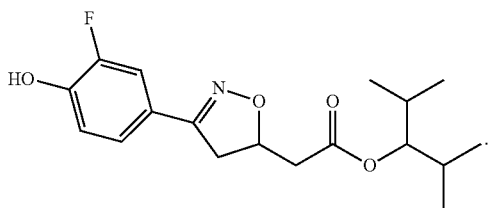 [SMILES: CC(C)C(OC(=O)CC1CC(c2ccc(O)c(F)c2)=NO1)C(C)C]

Still another preferred compound is ISO-60, having the formula

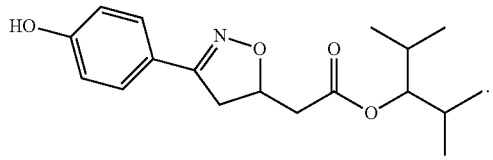 [SMILES: CC(C)C(OC(=O)CC1CC(c2ccc(O)cc2)=NO1)C(C)C]

In the most preferred embodiments, the compound is an (R) isomer.

An important discovery related to this invention is that addition of one or more fluorine moieties on the aromatic ring of isoxazoline MIF inhibitors improves the inhibitory activity. See Example 4. Thus, other isoxazoline MIF inhibitors, such as those disclosed in U.S. Patent Application Publication No. 2005-0250826 A1, would be expected to be improved by addition of one or more fluorine moieties on the aromatic ring. Thus, the invention is also directed to a compound of Formula II:

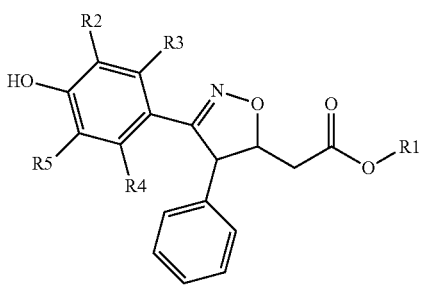

where R1 is a straight or branched $C_1$-$C_{10}$ alkyl, and R2, R3, R4 and R5 are independently F or H, provided that not all of R2, R3, R4 and R5 are H. Preferably, only one of R2, R3, R4 and R5 is F. More preferably, R2 is F. When R2 is F, it is preferred that R3, R4 and R5 are H.

The invention is also directed to pharmaceutical compositions comprising any of the above compounds, or a pharmaceutically acceptable salt thereof, in a pharmaceutically acceptable carrier.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be deter mined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The compounds can also be prepared for nasal administration. As used herein, nasal administration includes administering the compound to the mucous membranes of the nasal passage or nasal cavity of the patient. Pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

The compounds of the invention may be administered per se (neat) or in the form of a pharmaceutically acceptable salt. When used in medicine, the salts should be both pharmacologically and pharmaceutically acceptable, hut non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group.

The present invention is additionally directed to methods of inhibiting macrophage migration inhibitory factor (MIF) activity in a mammal. The methods comprise administering any of the above pharmaceutical compositions to the mammal in an amount effective to inhibit MIF activity in the mammal.

These methods can be used on any mammal. Preferably, the mammal is a human. It is also preferred that the mammal has or is at risk for a condition that comprises an inflammatory cytokine cascade that is at least partially mediated by an MIF. Non-limiting examples of such conditions include proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome and Hodgkins disease. A preferred such condition is sepsis, septicemia, and/or endotoxic shock.

MIF has been shown to play an important role in autoimmune disease. See, e.g., Cvetjovic et al., 2005. The present methods would thus be useful in treatment of autoimmune disease. Thus, in some aspect of these methods, the mammal has or is at risk for an autoimmune disease. Non-limiting examples of such autoimmune diseases are multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome and autoimmune inflammatory eye disease.

MIF also is known to promote tumor invasion and metastasis. See, e.g., Sun et al., 2005. The present methods would therefore be useful for treatment of a mammal that has a tumor.

The invention is also directed to methods of treating or preventing inflammation in a mammal. The methods comprise administering the above pharmaceutical composition to the mammal in an amount effective to treat or prevent the inflammation in the mammal.

For these methods, the mammal is preferably a human. The mammal can have, or be at risk for, a disease involving inflammation, for example proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome, or Hodgkins disease. Preferably, the mammal has sepsis, septicemia, and/or endotoxic shock, or is at risk for sepsis, septicemia, and/or endotoxic shock.

These methods can include the administration of a second anti-inflammatory agent to the mammal. Examples of such second anti-inflammatory agents are NSAIDs, salicylates, COX inhibitors, COX-2 inhibitors, and steroids. Preferably, the mammal has or is at risk for sepsis, septicemia, and/or endotoxic shock and the second treatment is administration of a muscarinic agonist, an adrenomedullin an adrenomedullin binding protein, a milk fat globule epidermal growth factor VIII, an activated protein C, or an α2A-adrenergic antagonist.

The present invention is also directed to methods of treating a mammal having sepsis, septicemia, and/or endotoxic shock. The methods comprise administering the above pharmaceutical composition to the mammal in an amount effective to treat the sepsis, septicemia and/or endotoxic shock.

The invention is further directed to methods of treating a mammal having an autoimmune disease. The methods comprise administering the above pharmaceutical composition to the mammal in an amount effective to treat the autoimmune disease. Examples of such autoimmune diseases include multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome and autoimmune inflammatory eye disease.

Additionally, the present invention is directed to methods of treating a mammal having a tumor, the method comprising administering the above pharmaceutical composition to the mammal in an amount effective to treat the tumor.

These compounds can be expected to be effectively administered orally. Thus, in any of the above methods, the pharmaceutical composition can be administered orally. Alternatively, the pharmaceutical composition can be administered parenterally.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Critical Modifications of the ISO-1 Scaffold Improve its Potent Inhibition of Macrophage Migration Inhibitory Factor (MIF) Activity Example Summary Based on the scaffold of (S,R)-3-(4-hydroxyphenyl)-4,5-dihydro-5-isoxazole acetic acid methyl ester (ISO-1), an inhibitor of the proinflammatory cytokine MIF, two critical modifications and chiral resolution have significantly improved the potency of the inhibition. (R)-17 is 20-fold more potent than ISO-1 and inhibits MIF tautomerase activity with an IC50 of 550 nM.

Results and Discussion

Figure 2:
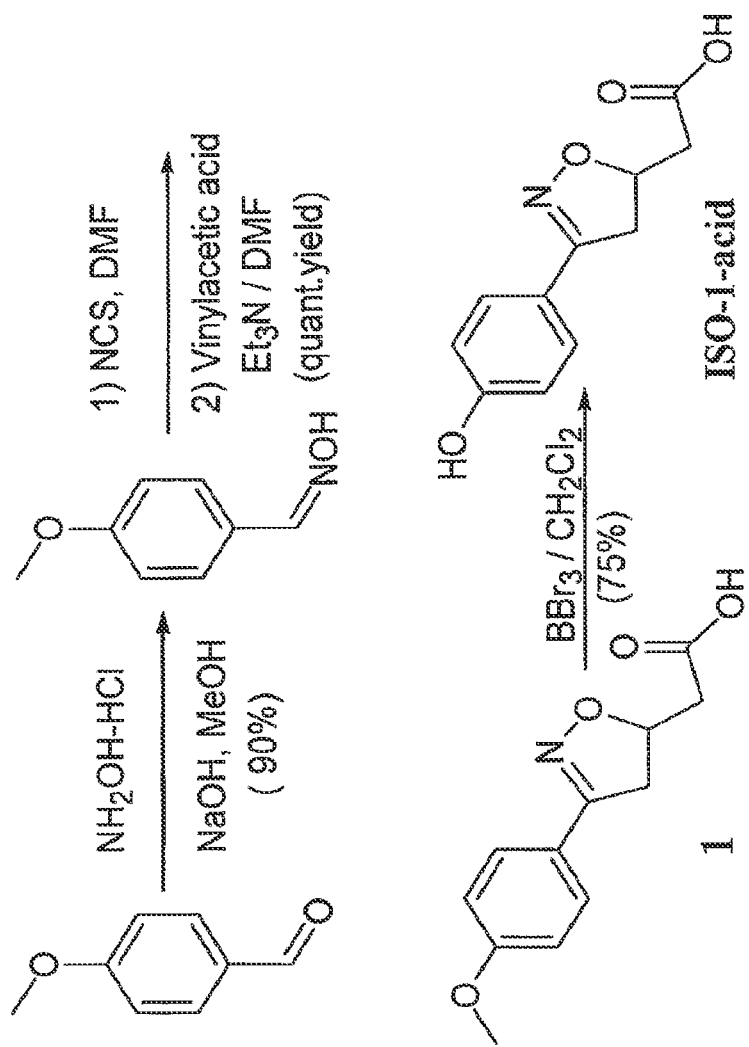
FIG. 2 shows a chemical scheme for the synthesis of the ISO-1-acid.
Figure 3:
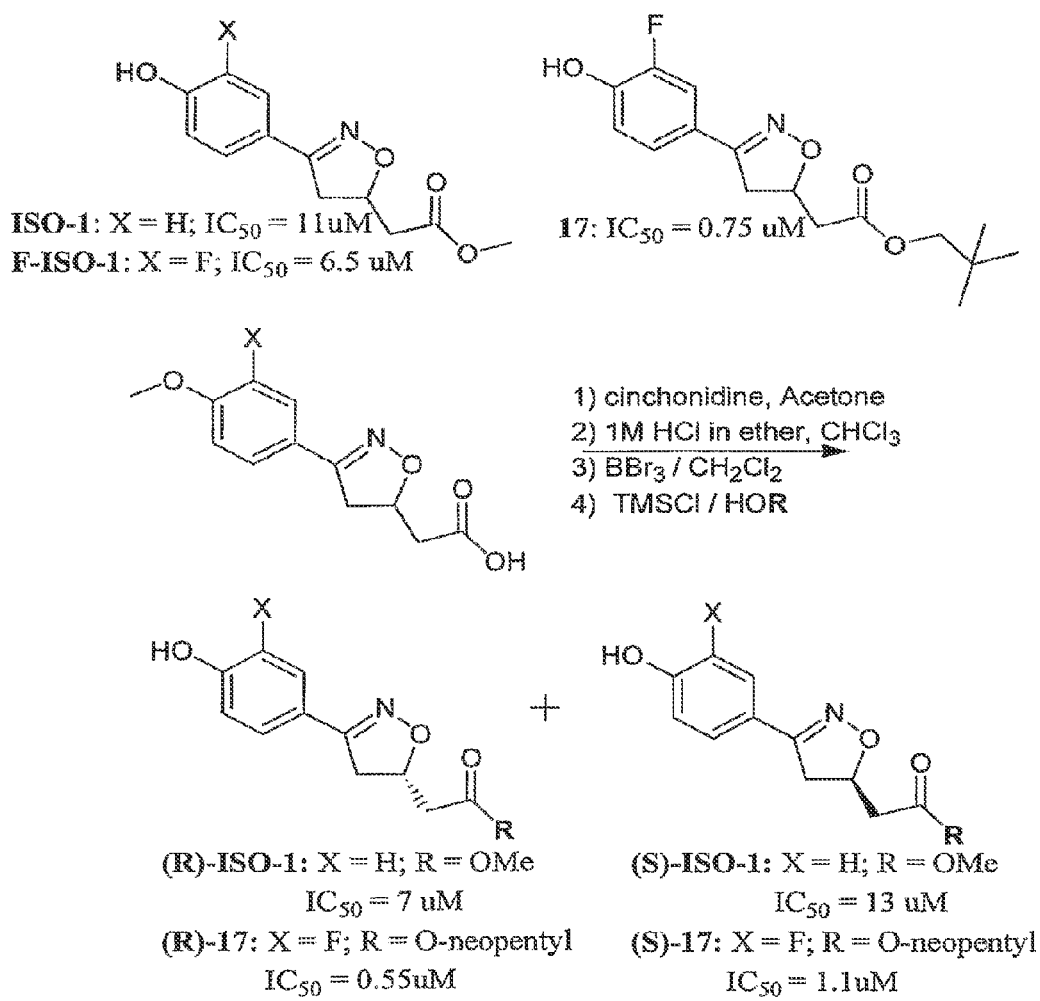
FIG. 3 shows a chemical scheme for the synthesis of stereoisomers of ISO-1 and Compound 17. The MIF inhibitory activity of the identified compounds is also provided.
Figure 4:
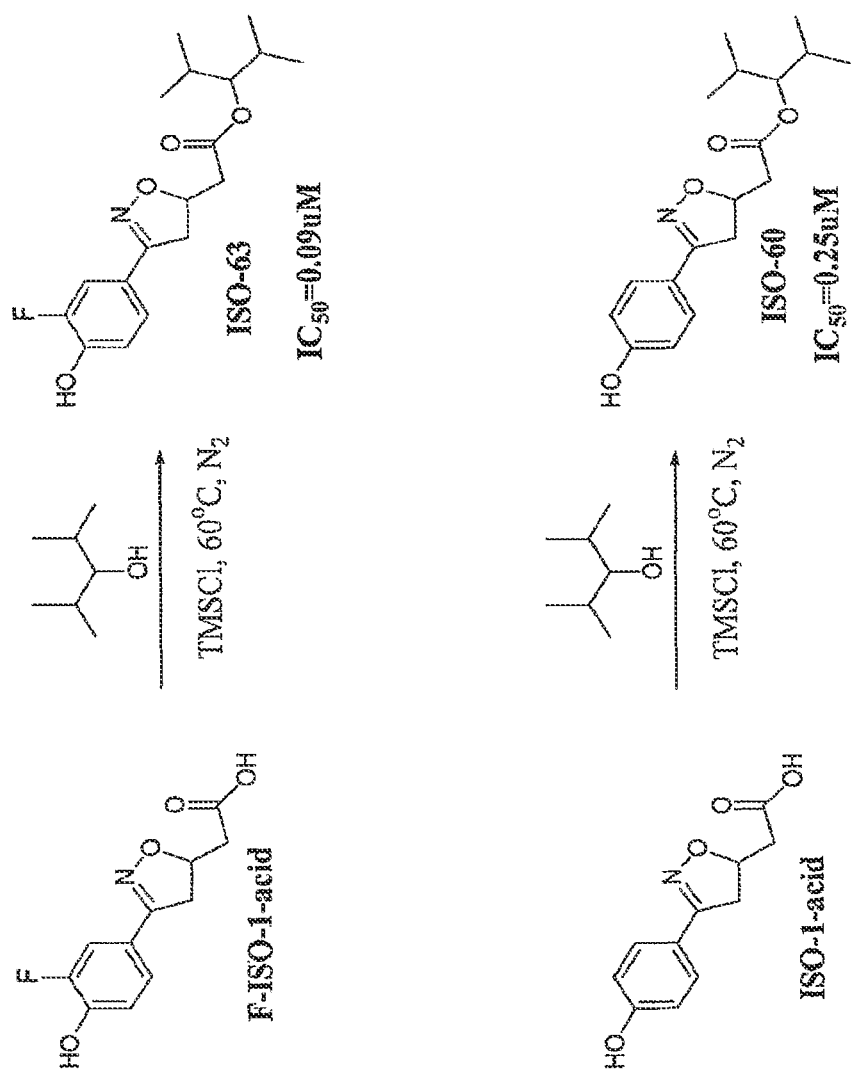
FIG. 4 shows a chemical scheme for the synthesis of two diisopropylmethylester isoxazoline compounds. The MIF inhibitory activity of the identified compounds is also provided.

To improve the potency of ISO-1, the structure-activity relationship of ISO-1 was explored. Previously, critical functional groups were identified within the ISO-1 scaffold as evident by the loss of its MIF inhibitory effect upon methylation of the para-hydroxyl functional group, oxidation of 4,5-dihydro-isoxazole to isoxazole or reduction of methyl ester to alcohol (Lubetsky et al., 2002). Herein, it was discovered that mono-fluorination onto the ortho position of the phenolic group of ISO-1 improved the inhibition of MIF activity up to 41% (FIG. 3). Also, the alkyl tail of ISO-1 was investigated with various ester and amide analogues. The new synthetic route provides the precursor (ISO-1-acid) in large scale (FIG. 2). Esterification and amide formation between the ISO-1-acid and alcohol (or amine) was accomplished using a standard DCC coupling protocol (DCC, DMAP or HOBt) (Table 1).

TABLE 1

Synthesis of Compounds 2-9.

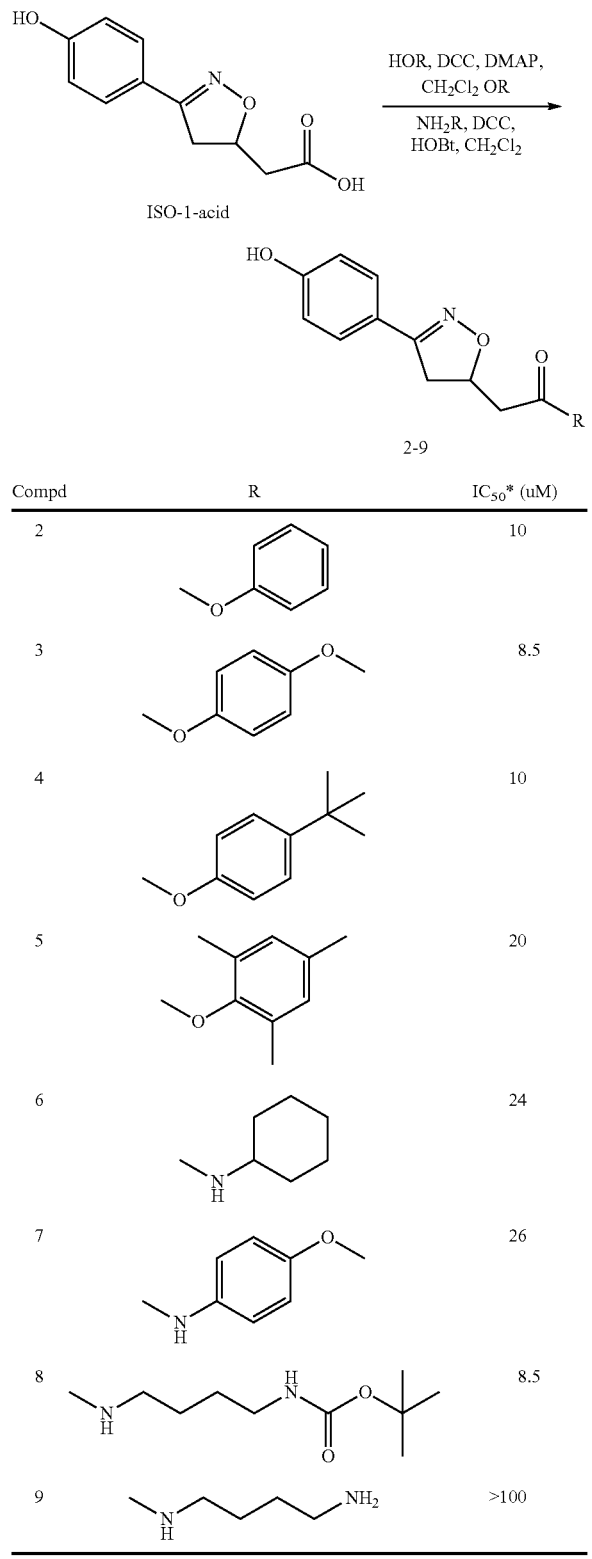

| Compd | R | IC$_{50}$* (uM) |
|---|---|---|
| 2 | (phenoxy) | 10 |
| 3 | (2,5-dimethoxyphenoxy) | 8.5 |
| 4 | (4-tert-butylphenoxy) | 10 |
| 5 | (2,4,6-trimethylphenoxy) | 20 |
| 6 | (N-methyl-N-cyclohexylamino) | 24 |
| 7 | (N-methyl-N-(4-methoxyphenyl)amino) | 26 |
| 8 | (N-methyl-N-(4-(Boc-amino)butyl)amino) | 8.5 |
| 9 | (N-methyl-N-(4-aminobutyl)amino) | >100 |

As summarized in Tables 1 and 2, we found that the ester analogues are more potent inhibitors than the amide counterpart (e.g. compounds 14 (IC$_{50}$=2.5 μM) vs. 6 (IC$_{50}$=24 μM) and 3 (IC$_{50}$=8.5 μM) vs. 7 (IC$_{50}$=26 μM)). We further investigated the influence of the bulkiness of the ester group on the potency of inhibiting MIF activity. The esterification process of ISO-1 acid was accomplished with TMSCl using the following alcohols: ethanol, 10; 1-propanol, 11; 2-propanol, 12; 1-butanol, 13; cyclohexanol, 14; cyclohexylmethanol, 15 and neopentylalcohol, 16 (Table 2). As shown in Table 3, the most bulky alcohol (compound 16, neopentyl ester analogue) shows a superior inhibition activity (IC$_{50}$=1.5 μM) which is about ten times more potent than ISO-1.

TABLE 2

Synthesis of Compounds 10-16.

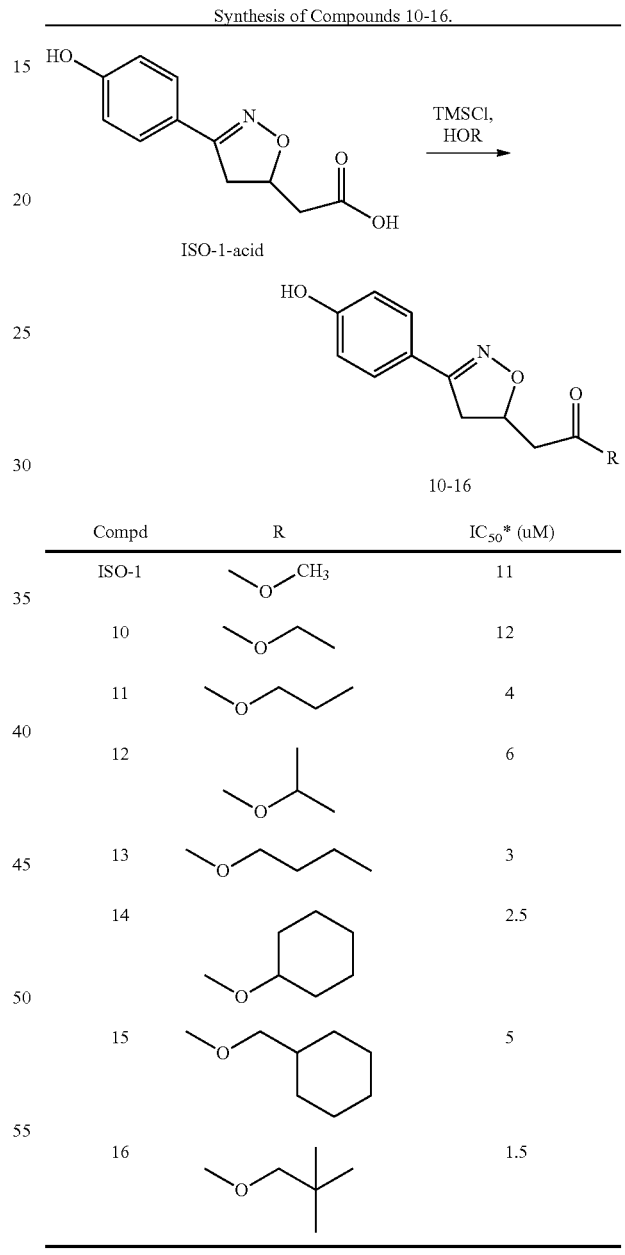

| Compd | R | IC$_{50}$* (uM) |
|---|---|---|
| ISO-1 | —O—CH$_3$ | 11 |
| 10 | —O—CH$_2$CH$_3$ | 12 |
| 11 | —O—CH$_2$CH$_2$CH$_3$ | 4 |
| 12 | —O—CH(CH$_3$)$_2$ | 6 |
| 13 | —O—CH$_2$CH$_2$CH$_2$CH$_3$ | 3 |
| 14 | —O—cyclohexyl | 2.5 |
| 15 | —O—CH$_2$-cyclohexyl | 5 |
| 16 | —O—CH$_2$C(CH$_3$)$_3$ | 1.5 |

The crystal structure analysis of MIF/ISO-1 complex predicts that the (R)-isomer of ISO-1 fits into the electron density better than (S)-isomer, suggesting that the (R)-isomer may bind with higher affinity to the MIF active site (Dios at al., 2002). Previously, the importance of the absolute configuration of the amino acid Schiff bases was shown for the inhibitory effect of MIF (Lubetsky et al., 2002). Hence, resolution of the optical active ISO-1 and determination of the inhibitory activity was needed for each isomer. Chiral resolution was accomplished as previously described through fractional crystallization of the diastereomeric cinchonidine salts of methylated ISO-1-acid (FIG. 3) (Wityak et al., 1997). The (S)-configuration salts were found to be less soluble and were crystallized out from the chiral mixture. The (S) and (R)-configuration salts were then acidified by 1N HCl, demethylated with $BBr_3$ and esterified with TMSCl in methanol to yield (S)-ISO-1 (90% cc) and (R)-ISO-1 (90% ee). Both isomers were tested for activity in an MIF dopachrome tautomerase assay, (R)-ISO-1 inhibited MIF tautomerase activity with an $IC_{50}$ of about 7 µM, but (S)-ISO-1 was 50% less active with an $IC_{50}$ of about 13 µM (FIG. 3).

In order to obtain the most potent, specific small molecule MIF inhibitor, three critical steps need to be integrated into the ISO-1 scaffold: (1) fluorination of the phenolic group of ISO-1, preferably mono-fluorination onto the ortho position of the phenolic group; (2) a bulkier functional group replacing the methyl ester of ISO-1, such as a neopentyl ester; and (3) chiral resolution obtain an (R)-isomer. Thus, compound 17 (FIG. 3) was optimized to be a potent inhibitor of MIF activity with an $IC_{50}$ of 750 nM. After the classical chiral resolution, (R)-17 inhibited MIF tautomerase activity with an $IC_{50}$ of 550 nM, while the (S)-17 was 50% less active with an $IC_{50}$ of about 1.1 µM (FIG. 3). Compound (R)-17 is 20 times more potent than the parent compound ISO-1.

After two critical modifications on ISO-1 scaffold, we have improved the inhibition of tautomerase activity to a nanomolar concentration (550 nM), which is about 20 times more potent than ISO-1.

Materials and Methods

MIF tautomerase activity was measured by UV-Visible recording spectrophotometry (SHIMADZU, UV1600U). A fresh stock solution of L-dopachrome methyl ester was prepared at 2.4 mM through oxidation of L-3,4-dihydroxyphenylalanine methyl ester with sodium periodate. 1 µL of MIF solution (800-900 ng/mL) and 1 µL of a DMSO solution with various concentrations of the enzymatic inhibitor were added into a plastic cuvette (10 mm, 1.5 mL) containing 0.7 mL assay buffer (50 mM potassium phosphate, pH 7.2). Then L-dopachrome methyl ester solution (0.3 mL) was added to the assay buffer mixture. Activity was determined at room temperature and the spectrometric measurements were made at $\lambda=475$ nm for 20 seconds by monitoring the rate of decolorization of L-dopachrome methyl ester in comparison to a standard solution.

All solvents were HPLC-grade from Fisher Scientific. Silica gel (Selecto Scientific, 32-63 µm average particle size) was used for flash column chromatography (FCC). Aluminum-backed Silica Gel 60 with a 254 nm fluorescent indicator TLC plates were used. Spots on TLC plates were visualized under a short wavelength UV lamp or stained with $I_2$ vapor. NMR spectra were preformed on a Jeol Eclipse 270 spectrometer at 270 MHz for $^1H$ NMR spectra and 67.5 MHz for the $^{13}C$ NMR spectra. Coupling constants are reported in Hertz (Hz), and chemical shifts are reported in parts per million (ppm) relative to deuterated solvent peak. The coupling constants (J) are measured in Hertz (Hz) and assigned as s (singlet), d (doublet), t (triplet), m (multiplet) and br (broad). Low-resolution mass spectra were acquired using Thermofinnigan LCQ DecaXPplus quadrupole ion trap MS with negative-ion or positive-ion mode.

Preparation of 4-Methoxybenzaldehyde Oxime

To a solution of 4-methoxybenzaldehyde (5.0 g, 36.8 mmol) in methanol (300 mL) was added hydroxylamine hydrochloride (7.6 g, 110.4 mmol) and 2N NaOH (37 mL, 73.6 mmol). The mixture was stirred at room temperature for 6 hours. The mixture was neutralized to pH 4 by using 1N HCl. Excess methanol was removed in vacuo to precipitate out the oxime. The precipitations were filtered and washed with water. The product was dried under vacuum and yield a white solid (4.9 g, 88%): $^1H$ NMR (270 MHz, acetone-$d_6$) δ 8.07 (s, 1H), 7.55 (d, J=8.2 Hz, 2H), 6.95 (d, J=8.2 Hz, 2H), 3.82 (s, 3H).

Preparation of ISO-1-Acid.

To a solution of 4-methoxybenzaldoxime (4 g, 26 mmol) in anhydrous DMF (500 mL) was added NCS (5.2 g, 39 mmol). The reaction mixture was stirred for 5 hours at RT affording the chloro ovine. To this solution, vinylacetic, acid (6.6 mL, 78 mmol) was added, followed by the dropwise addition of triethylamine (5.5 mL, 39 mmol) DMF (50 mL). The reaction mixture was stirred under $N_2$ at RT for 48 hours. The solvent was removed in vacuo and the residue was taken up in EtOAc. The EtOAc solution was washed with 0.5N HCl, water, brine, and dried with anhydrous $MgSO_4$. The final solution was concentrated in vacuo and dried under vacuum pump to afford 1 in quantitative yield. To a solution of 1 (40-50 mM, in dry dichloromethane) was treated with an excess (8-10 equivalence) of boron tribromide (1M solution in dichloromethane, Aldrich cat #: 211222) at 0° C. under $N_2$. The reaction mixture was allowed to reach room temperature over 5-6 hrs and then quenched with aqueous saturated $NaHCO_3$ (caution: $BBr_3$ reacts violently with water!!!). The mixture was stirred for ½ hr and then diluted with water and $CH_2Cl_2$. The organic layer was separated from the aqueous layer and discarded. The aqueous portion was neutralized with 1N HCl to pH 4 and extracted with EtOAc. The combined EtOAc solution was washed with brine and dried with anhydrous $MgSO_4$ to afford ISO-1-acid as pale yellow powder in good yield (75%). $^1H$ NMR (300 MHz, acetone-$d_6$) δ 10.65 (br, 1H), 8.75 (s, 1H), 7.52 (d, J=8.7 Hz, 2H), 6.35 (d, J=8.7 Hz, 2H), 5.01 (m, 1H), 3.50 (m, 1H), 3.05 (m, 1H), 2.68 (m, 2H); ESI-MS m/z 220 ($M^-$).

General DCC Coupling Procedure for Formation of Esters or Amides

To a solution of ISO-1-acid (100 mM in dry dichloromethane) was treated with 1.1 equivalences DCC, 0.2 equivalences DMAP and 1.5 equivalences alcohols (or 0.2 equivalences HOBt and 1.5 equivalences amines). The mixture was stirred for 8 hrs at RT. The formed white precipitate was filtered off and washed with $CH_2Cl_2$ and the filtrate was evaporated to dryness. The residue was purified on silica gel (hexane/EtOAc/MeOH 4/3/1) to give the esters or amides as a white solid. Compound 2 (65% yield): $^1H$ NMR (300 MHz, acetone-$d_6$) δ 8.75 (br, 1H), 7.54 (d, J=8.7 Hz, 2H), 7.38 (m, 2H), 7.22 (m, 1H), 7.11 (m, 2H), 6.86 (d, J=8.7 Hz, 2H), 5.10 (m, 1H), 3.54 (m, 1H), 3.27 (m, 1H), 2.96 (m, 2H); ESI-MS m/z 296 ($M^-$). Compound 3 (60% yield): $^1H$ NMR (300 MHz, acetone-$d_6$) δ 8.78 (s, 1H), 7.52 (d, J=8.7 Hz, 2H), 7.02 (d, J=8.7 Hz, 2H), 6.90 (d, J=8.7 Hz, 2H), 6.86 (d, J=8.7 Hz, 2H), 5.10 (m, 1H), 3.76 (s, 3H), 3.53 (m, 1H), 3.25 (m, 1H), 2.76 (m, 2H); ESI-MS m/z 326 ($M^-$). Compound 4 (40% yield): $^1H$ NMR (300 MHz, acetone-$d_6$) δ 8.75 (br, 1H), 7.55 (d, J=8.7 Hz, 2H), 7.39 (d, J=8.7 Hz, 2H), 7.03 (d, J=8.7 Hz, 2H), 6.85 (d, J=8.7 Hz, 2H), 5.11 (m, 1H), 3.55 (m, 1H), 3.23 (m, 1H), 2.95 (m, 2H), 1.30 (s, 9H); ESI-MS m/z 352 ($M^-$). Compound 5 (30% yield): $^1H$ NMR (300 MHz, acetone-$d_6$) δ 8.75 (s, 1H), 7.72 (d, J=8.7 Hz, 2H), 7.17 (d, J=8.7 Hz, 2H), 6.86 (s, 2H), 5.10 (m, 1H), 3.55 (m, 1H), 3.25 (m, 1H), 2.96 (m, 2H), 2.05 (s, 9H); ESI-MS m/z 338 ($M^-$). Compound 6 (80% yield): $^1H$ NMR (300 MHz, acetone-$d_6$) δ 8.79 (s, 1H), 7.52 (d, J=8.7 Hz, 2H), 7.00 (br, 1H), 6.85 (d, J=8.7 Hz, 2H), 4.94 (m, 1H), 3.64 (m, 1H), 3.42 (m, 1H), 3.10 (m, 1H), 2.52

(m, 1H), 2.37 (m, 1H) 1.90-1.00 (m, 10H); ESI-MS m/z 301 (M⁻). Compound 7 (88% yield): ¹H NMR (300 MHz, acetone-d₆) δ 9.10 (br, 1H), 8.80 (br, 1H), 7.53 (m, 4H), 6.84 (m, 4H), 5.06 (m, 1H), 3.72 (s, 3H), 3.49 (m, 1H), 3.17 (m, 1H), 2.73 (m, 1H), 2.60 (m, 1H); ESI-MS m/z 325 (M⁻). Compound 8 (95% yield) ¹H NMR (270 MHz, acetone-d₆) δ 7.52 (d, J=8.7 Hz, 2H), 6.88 (d, J=8.7 Hz, 2H), 6.07 (br, 1H), 5.02 (m, 1H), 3.46 (m, 1H), 3.13 (m, 5H), 2.56 (m, 2H), 1.51 (m, 4H), 1.38 (s, 9H); ESI-MS m/z 414 (M+Na⁺). Compound 9 (90% yield) ¹H NMR (270 MHz, acetone-d₆) δ 8.63 (br, 1H), 7.52 (d, 8.7 Hz, 2H), 6.87 (d, J=8.7 Hz, 2H), 5.04 (m, 1H), 3.84 (m, 2H), 3.28 (m, 3H), 2.58 (m, 3H), 1.86 (m, 2H), 1.65 (m, 2H); ESI-MS m/z 292 (M⁺).

General TMSCl Esterification Procedure.

To a solution of ISO-1-acid (50 mg, 0.23 mmol) in a 3 mL, alcohol (ethanol, 10; 1-propanol, 11; 2-propanol, 12; 1-butanol, 13; cyclohexanol, 14; cyclohexylmethanol, 15 and neopentylalcohol, 16) was added 0.1 mL TMSCl. The mixture was stirred for 2 hrs at RT (for 14, 15 and 16: 3 hrs at 50° C.). The mixture was evaporated to dryness and the residue was subjected to purification on silica gel (hexane/EtOAc 4/3) to afford white solid or pale yellow oil in quantitative yield. Compound 10: ¹H NMR (300 MHz, acetone-d₆) δ 8.74 (s, 1H), 7.52 (d, J=8.7 Hz, 2H), 6.85 (d, J=8.7 Hz, 2H), 4.97 (m, 1H), 4.10 (q, 2H), 3.51 (m, 1H), 3.12 (m, 1H), 2.66 (m, 2H) 1.19 (t, 3H); ESI-MS m/z 248 (M⁻). Compound 11: ¹H NMR (300 MHz, acetone-d₆) δ 8.75 (s, 1H), 7.51 (d, J=8.7 Hz, 2H), 6.86 (d, J=8.7 Hz, 2H), 4.98 (m, 1H), 4.01 (t, 2H), 3.51 (m, 1H), 3.15 (m, 1H), 2.66 (m, 2H) 1.60 (m, 2H), 0.89 (t, 3H); ESI-MS m/z 262 (M⁻). Compound 12: ¹H NMR (300 MHz, acetone-d₆) δ 8.74 (s, 1H), 7.51 (d, J=8.7 Hz, 2H), 6.85 (d, J=8.7 Hz, 2H), 4.97 (m, 2H), 4.72 (m, 1H), 3.51 (m, 1H), 3.12 (m, 1H), 2.63 (m, 2H) 1.18 (d, J=6.3 Hz, 6H); ESI-MS m/z 262 (M⁻). Compound 13: ¹H NMR (300 MHz, acetone-d₆) δ 8.78 (s, 1H), 7.52 (d, J=8.7 Hz, 2H), 6.86 (d, J=8.7 Hz, 2H), 4.99 (m, 1H), 4.05 (t, 2H), 3.51 (m, 1H), 3.12 (m, 1H), 2.68 (m, 2H) 1.10-1.60 (m, 4H), 0.88 (t, 3H); ESI-MS m/z 276 (M⁻). Compound 14: ¹H NMR (300 MHz, acetone-d₆) δ 8.84 (br, 1H), 7.52 (d, J=8.7 Hz, 2H), 6.86 (d, J=8.7 Hz, 2H), 4.98 (m, 1H), 4.72 (m, 1H), 3.51 (m, 1H), 3.15 (m, 1H), 2.66 (m, 2H) 1.90-1.20 (m, 10H); ESI-MS m/z 302 (M⁻). Compound 15: ¹H NMR (300 MHz, acetone-d₆) δ 8.78 (s, 1H), 7.55 (d, J=8.7 Hz, 2H), 6.88 (d, J=8.7 Hz, 2H), 5.02 (m, 1H), 3.90 (d, J=6.7 Hz, 2H), 3.51 (m, 1H), 3.15 (m, 1H), 2.72 (m, 2H) 1.80-0.90 (m, 11H); ESI-MS m/z 302 (M⁻). Compound 16: ¹H NMR (300 MHz, acetone-d₆) δ 8.79 (s, 1H), 7.54 (d, J=8.7 Hz, 2H), 6.88 (d, J=8.7 Hz, 2H), 5.05 (m, 1H), 3.82 (m, 2H), 3.52 (m, 1H), 3.18 (m, 1H), 2.75 (m, 2H) 0.96 (s, 9H); ESI-MS m/z 292 (M⁺).

Classical Resolution of Acid 1 Via Crystallization of the Cinchonidine Salts.

(R,S)-1 (1.3 g, 5.5 mmol) was dissolved in hot acetone (25 mL), cinchonidine (1.61 g, 5.5 mmol) was added, and the solution was cool to RT and allowed to stand at −20° C. overnight. The resulting white solid was filtered to give (S)-1 salts. The filtrate was concentrated in vacuo to afford (R)-1 salts. To a solution of (R)-1 salts or (S)-1 salts (200 mg, 0.4 mmol) in chloroform (3 mL) was added 1N HCl in ether (3 mL, 3 mmol). The resulting white precipitate was filtered off and the filtrate was concentrated in vacuo to give (R)-1 or (S)-1 in quantitative yield.

EXAMPLE 2

Effect of Isoxazoline MIF Inhibitors on Leukocyte Recruitment in Response to Acute Inflammation Air pouches were made according to standard procedures (Garcia-Ramallo et al., 2002) on Swiss Webster male mice (25-30 g) by injecting sterile air s.c. on day 0 (6 ml) and day 3 (3 ml). On day 6, animals were treated with a single i.p. injection with either vehicle (350 μl of 20% DMSO), ISO-1 (40 mg/kg), or ISO-63 (40 mg/kg). After 15 min, the animals were challenged by injecting 1 ml 1% carrageenan (in PBS) into the air pouch cavity. Five hr after carrageenan injection the animals were sacrificed, the pouches washed with PBS, exudate collected, and the total number of infiltrating cells quantitated.

Figure 5:
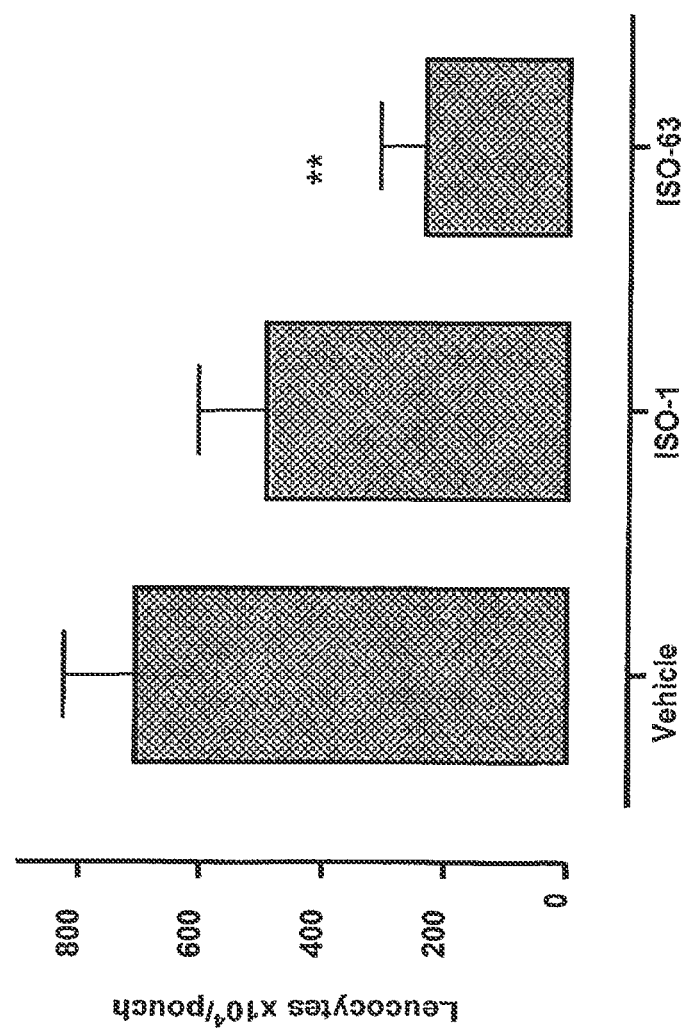
FIG. 5 is a graph of experimental results showing that ISO-63 inhibits leukocyte recruitment in an established model of acute inflammation. ** $p<0.007$ (n 7) relative to vehicle alone.

FIG. 5 summarizes the results of this assay. The ISO-63 treatment, but not the ISO-1 treatment, caused a significant reduction in leukocyte recruitment in response to acute inflammation.

EXAMPLE 3

Effect of Isoxazoline MIF Inhibitors on Invasion of Rheumatoid Arthritis Fibroblast-Like Synoviocytes (RA-FLS) into Matrigel Invasion was assayed by measuring cell invasion through Matrigel Invasion Chambers (Becton Dickinson, Mass.). One day after treatment of RA-FLS with 25 μM ISO-1 or 100 nM ISO-63, 4×10⁴ cells were placed in the upper chamber in serum-free medium. 500 μl of whole medium containing 10% FBS and 10% human serum and was added to the bottom chamber. After 24 hours of incubation at 37° C., cells on the upper surface of the filter were wiped off with a Q-tip and the filter was fixed in 4% formaldehyde/PBS. After staining with crystal violet, migrated cells were counted using an inverted microscope.

Figure 6:
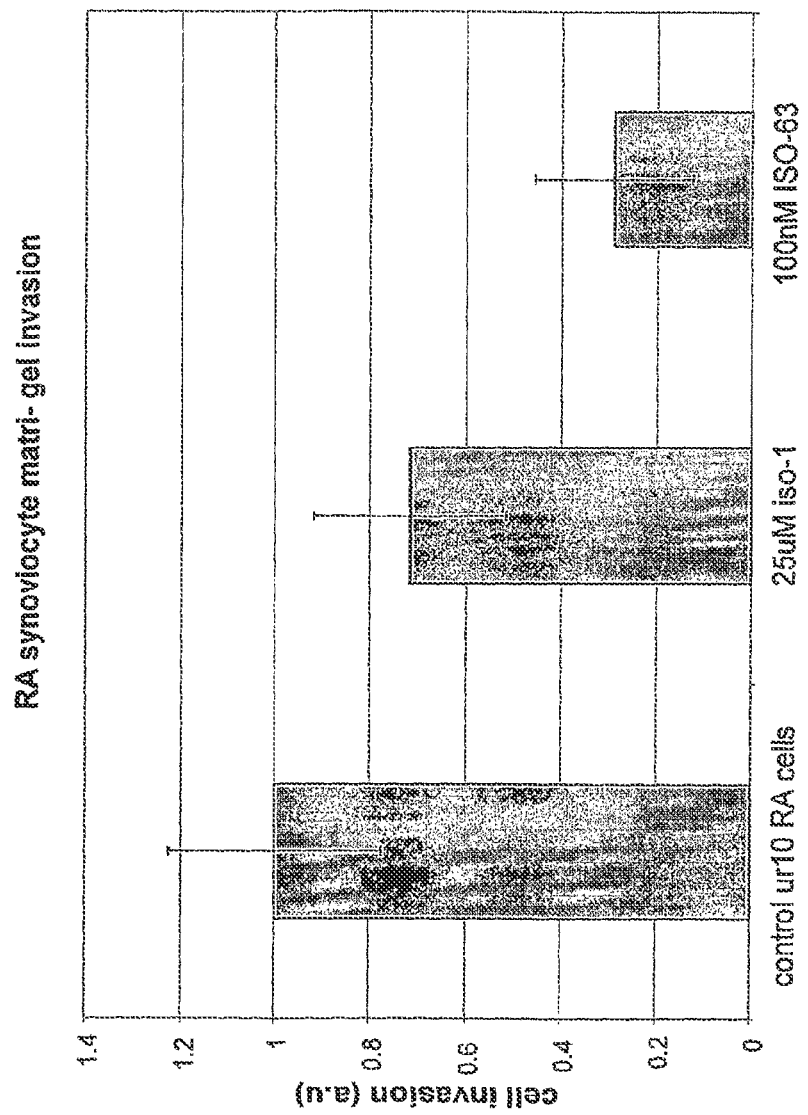
FIG. 6 is a graph of experimental results showing that ISO-63 inhibits the invasion of rheumatoid arthritis fibroblast-like synoviocytes (RA-FLS) into Matragel.

FIG. 6 summarizes the results of this assay. The ISO-63 treatment reduced cell invasion to a much greater extent than the ISO-1 treatment.

REFERENCES

Al-Abed, Y.; Dabideen, D.; Aljabari, B.; Valster, A.; Messmer, D.; Ochani, M.; Tanovic, M.; Ochani, K.; Bacher, M.; Nicoletti, F.; Metz, C.; Pavlov, V. A.; Miller, E. J.; Tracey, K. J. *J. Biol. Chem.* 2005, 280, 36541.

Calandra, T.; Roger, T. *Nat Rev Immunol* 2003, 3, 791.

Cvetkovic, I; Al-Abed, Y. et al. Critical role of macrophage migration inhibitory factor activity in experimental autoimmune diabetes. *Endocrinol.* 2005, 146, 2942-2951.

Dios, A.; Mitchell, R. A.; Aljabari, B.; Lubetsky, J.; O'Connor, K.; Liao, H.; Senter, P. D.; Manogue, K. R.; Lolis, E.; Metz, C.; Bucala, R.; Callaway, D. J. E.; Al-Abed, Y. *J. Med. Chem.* 2002, 45, 2410.

Garcia-Ramallo E.; Marques, T. et al. Resident cell chemokine expression serves as the major mechanism for leukocyte recruitment during local inflammation. *J. Immunol.* 2002, 169, 6467-6473

Lin, X.; Sakuragi, T.; Metz, C.; Ojamaa, K.; Skopicki, H. A.; Wang, P.; Al-Abed, Y.; Miller, E. J. *Shock* 2005, 24, 556.

Lubetsky, J. B.; Dios, A.; Han, J.; Aljabari, B.; Ruzsicska, B.; Mitchell, R.; Lolis, E.; Al-Abed, Y. *J. Biol. Chem.* 2002, 277, 24976.

Riedemann, N. C.; Guo, R. F.; Ward P. A. *Nat Med* 2003, 9, 517.

Sun, B.; Nishihira, J. et al. Macrophage migration inhibitory factor promotes tumor invasion and metastasis via the Rho-dependent pathway. *Clin. Cancer Res.* 2005, 11, 1050-1058.

Wityak, J.; Sielecki, T. M.; Pinto, D. J.; Emmett, G.; Sze, J. Y.; Liu, J.; Tobin, A. E.; Wang, S.; Jiang, B.; Ma, P.; Mousa, S. A.; Wexler, R. U.; Olson, R. E. *J. Med. Chem.* 1997, 40, 50.

U.S. Patent Application No. 2005-0250826 A 1.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having the structure:

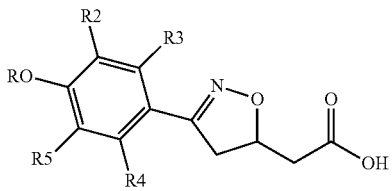

I wherein R2, R3, R4 and R5 are independently F or H, wherein at least one of R2, R3, R4 and R5 is F and R is H or CH$_3$.

2. The compound of claim 1, wherein R2 is F.

3. The compound of claim 1, having the formula:

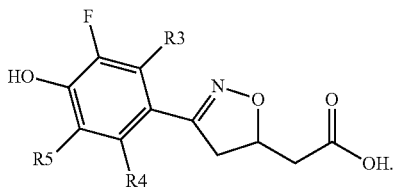

4. The compound of claim 1, having the formula

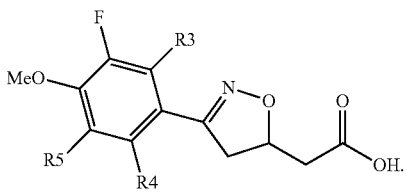

5. A pharmaceutical composition comprising the compound of claim 1 in a pharmaceutically acceptable excipient.

6. The compound of claim 1, which is an (R) isomer.

* * * * *